United States Patent [19]
Beale et al.

[11] Patent Number: 5,889,040
[45] Date of Patent: *Mar. 30, 1999

[54] COMPOSITION FOR INCREASING PROTEIN CONCENTRATION IN A MAMMAL

[75] Inventors: Paxton K. Beale, 1801 Bush St. Suite 300, San Francisco, Calif. 94109; Donald O. Nickey, Plain City, Ohio

[73] Assignee: Paxton K. Beale, San Francisco, Calif.

[ * ] Notice: The term of this patent shall not extend beyond the expiration date of Pat. No. 5,716,926.

[21] Appl. No.: 951,547

[22] Filed: Oct. 16, 1997

Related U.S. Application Data

[63] Continuation of Ser. No. 686,819, Jul. 26, 1996, Pat. No. 5,716,926.

[51] Int. Cl.$^6$ .................................................. A61K 31/415
[52] U.S. Cl. ...................... 514/400; 514/419; 514/423; 514/561; 514/562; 514/564; 514/567
[58] Field of Search ..................... 514/561, 400

[56] References Cited

U.S. PATENT DOCUMENTS

| | | | |
|---|---|---|---|
| 4,042,688 | 8/1977 | Gans et al. | 514/21 |
| 4,351,835 | 9/1982 | Stanko | 424/252 |
| 4,415,576 | 11/1983 | Stanko | 514/251 |
| 4,548,937 | 10/1985 | Stanko | 514/251 |
| 4,645,764 | 2/1987 | Stanko | 514/251 |
| 4,687,782 | 8/1987 | Brantman | 514/561 |
| 4,812,479 | 3/1989 | Stanko | 514/557 |
| 4,871,550 | 10/1989 | Millman | 514/23 |
| 4,874,790 | 10/1989 | Stanko | 514/557 |
| 4,981,687 | 1/1991 | Fregley et al. | 424/439 |
| 4,988,515 | 1/1991 | Buckberg | 514/23 |
| 5,026,721 | 6/1991 | Dudrick et al. | 514/396 |
| 5,028,440 | 7/1991 | Nissen | 426/2 |
| 5,087,472 | 2/1992 | Nissen | 426/623 |
| 5,089,477 | 2/1992 | Fregley et al. | 514/23 |
| 5,134,162 | 7/1992 | Stanko | 514/557 |
| 5,143,842 | 9/1992 | Ham et al. | 435/387 |
| 5,147,650 | 9/1992 | Fregley et al. | 424/439 |
| 5,183,674 | 2/1993 | Olin | 426/69 |
| 5,236,712 | 8/1993 | Fregly et al. | 424/439 |
| 5,238,684 | 8/1993 | Fregly et al. | 424/439 |
| 5,256,697 | 10/1993 | Miller et al. | 514/625 |
| 5,283,260 | 2/1994 | Miller et al. | 514/563 |
| 5,294,606 | 3/1994 | Hastings | 514/53 |
| 5,294,641 | 3/1994 | Stanko | 514/540 |
| 5,312,985 | 5/1994 | Dhaon et al. | 564/143 |
| 5,348,979 | 9/1994 | Nissen et al. | 514/557 |
| 5,360,613 | 11/1994 | Nissen | 424/439 |
| 5,428,072 | 6/1995 | Cook et al. | 514/560 |
| 5,430,066 | 7/1995 | Cook et al. | 514/558 |
| 5,472,980 | 12/1995 | Miller | 514/563 |
| 5,480,909 | 1/1996 | Stanko | 514/557 |
| 5,508,308 | 4/1996 | Miller et al. | 514/563 |
| 5,536,751 | 7/1996 | Bunger | 514/557 |
| 5,719,119 | 2/1998 | Veech | 514/2 |

OTHER PUBLICATIONS

Reiners et al. Cereal Chem., 47(2), 205–6, 1970.

*Primary Examiner*—Leonard Schenkman
*Attorney, Agent, or Firm*—Donald O. Nickey; Standley & Gilcrest

[57] ABSTRACT

The present invention is based in part upon the discovery that the use of pyruvate in enteral formulations, in combination with an anabolic protein composition, produces a synergistic effect in increasing the lean body mass or muscle tissue of a mammal consuming same. The present invention also provides a method for enhanced endurance of athletes.

The present invention relates generally to a composition for enhancing the protein concentration or muscle mass of a mammal and a method for enhancing the protein concentration or muscle mass in a mammal. More specifically, the present invention relates to a composition which comprises pyruvate and/or derivatives of pyruvate and an anabolic protein composition. The method of the present invention comprises administering to a mammal in need of enhancing its protein concentration or muscle mass, a composition comprising pyruvate and an anabolic protein composition.

The pyruvate/anabolic protein composition can take the form of powders, liquids, pills, capsules, tablets, food additives, candies or confections.

1 Claim, No Drawings

COMPOSITION FOR INCREASING PROTEIN CONCENTRATION IN A MAMMAL

This application is a continuation of application Ser. No. 08/686,819 filed Jul. 26, 1996, U.S. Pat. No. 5,716,926.

TECHNICAL FIELD

The present invention relates generally to a composition for and method of enhancing the protein concentration or muscle mass of a mammal. More specifically, the present invention relates to a composition which comprises pyruvate and/or derivatives of pyruvate and a novel blend of proteins and/or amino acids that possesses an amino acid profile that is similar to the amino acid profile of human muscle tissue. The method of the present invention comprises administering to a mammal in need of enhancing its protein concentration or muscle mass, a composition comprising pyruvate and a source of amino nitrogen having specific types and levels of amino acids. The method of this invention results in a synergistic increase of muscle mass while at the same time lowering the deposition of body fat.

BACKGROUND ART

Athletes engage in strenuous training to accomplish the goals of their sport. This strenuous training essentially amounts to trauma to the body, in that the human body interprets every strenuous work-out as a threat to its survival. It is known that muscle damage, caused by training, releases the catabolic hormone prostaglandin-E2. Training also causes the release of adrenocorticotropin (ACTH), which is a pituitary hormone. The presence of increased levels of ACTH increases the production of the catabolic hormone cortisol. Cortisol is also known as hydrocortisone, which is a glucocorticoid of the adrenal cortex that is a derivative of cortisone and is used in the treatment of rheumatoid arthritis. Thus, cortisol is a naturally occurring anti-inflammatory steroid. This catabolic hormone results in the release of amino acids from muscle tissue and prevents absorption of glucose. Cortisol, as a catabolic stress hormone, cannibalizes muscle tissue. High cortisol levels also result in the breakdown of connective tissue, lowered immunity and reduced muscle RNA synthesis. While cortisol may be a detriment to the athlete, scientists have conjectured that when the human body is stressed or traumatized, it triggers a "fight or flight" survival response. The biological design of cortisol is such that when a human is threatened, cortisol levels rise and mobilize the body for action by breaking down fat and muscle stores for emergency energy. Cortisol also reduces swelling in the event of injury. After the threat or trauma has subsided, cortisol levels return to normal. The cortisol-stress relationship is designed for intermittent physical threats and not the constant stimulation provided by today's aggressive athletes. Ongoing training results in cortisol levels that do not return to normal for extended periods of time and thereby result in the breakdown or loss of muscle tissue.

After strenuous exercise, muscle tissue enters a stage of rapid nitrogen absorption in the form of amino acids and small peptides in order to rebuild the muscle fibers, grow and add new muscle fibers. During this period of repair and growth, it is important that the muscle cells have available to them sufficient levels of nitrogen in the form of amino acids. While the total level of amino nitrogen is important, the ratios of the various amino acids is even more important.

Athletes that over-train sometimes enter into a catabolic condition. Muscle catabolism occurs when the athlete enters a negative nitrogen balance. People on diets usually have a negative nitrogen balance and therefore lose muscle when they lose weight. In contrast, a positive nitrogen balance means the animal has enough nitrogen left over to synthesize muscle proteins.

Various organizations have propounded a list of essential amino acids which are required on a daily basis for proper nutrition. These amino acid requirements vary throughout the growth cycle of all animals. Human muscle tissue is made up of specific amino acids and at specific ratios. If any of these amino acids are missing or deficient, the muscles will not grow, will grow slowly and may even begin to breakdown. However, if the animal is supplied with adequate amounts of protein that contain all of the muscle amino acids, this protein or source of amino nitrogen will be able to support rapid muscle recovery and growth.

The amino acids leucine, isoleucine and valine are the branched chain amino acids and are necessary for a positive nitrogen balance and muscle growth. The branched chain amino acids are lost at significant levels during strenuous exercise and therefore it is critical that they be available during the anabolic state.

The present invention is based in part, upon the discovery that the use of pyruvate in combination with an anabolic protein composition, produces a synergistic effect in increasing the lean body mass or muscle tissue of a mammal consuming same while at the same time decreasing the deposition of fat in the body.

As used herein and the claims, the term "pyruvate" means any salt or ester of pyruvic acid. Pyruvic acid has the formula:

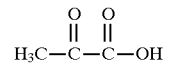

Pyruvic acid is a colorless liquid with an odor resembling that of acetic acid and has a melting point of 13° C. Pyruvic acid is an intermediate in the breakdown of sugars to alcohol by yeast. The mineral salts of pyruvic acid, such as magnesium pyruvate or calcium pyruvate or mixtures thereof are useful in the present invention. Sodium pyruvate is not especially preferred as it is known that sodium is associated with various negative medical conditions such as high blood pressure, water retention and heart disease. Further, certain athletes, such as bodybuilders, desire to present a defined visual image of their body which shows muscle definition and thus, the water retention properties of the sodium salt are not beneficial. Pyruvate precursors in the form of pyruvamides or pyruvyl-amino acids are also useful in the present invention. Pyruvyl-glycine is representative of the useful pyruvyl-amino acids.

Pyruvate has a number of useful applications in medicine. Pyruvate has been described for retarding fatty deposits in livers (U.S. Pat. No. 4,158,057); for treating diabetes (U.S. Pat. No. 4,874,790); for retarding weight gain (U.S. Pat. Nos. 4,812,879, 4,548,937, and 4,351,835); to increase body protein concentrations in a mammal (U.S. Pat. No. 4,415,576); for treating cardiac patients to increase the cardiac output without accompanying increase in cardiac oxygen demand (U.S. No. Pat. 5,294,641); for extending athletic endurance (U.S. Pat. No. 4,315,835); for retarding cholesterol increase (U.S. Pat. No. 5,134,162); for inhibiting growth and spread of malignancy and retarding DNA breaks (U.S. application Ser. No. 08/194,857 filed February 14, 1994); and for inhibiting generation of free radicals (U.S. application Ser. No. 08/286,946 filed Aug. 8, 1994). All of these references are incorporated herein by reference.

U.S. Pat. 4,981,687 discloses compositions and methods for achieving improved physiological response to exercise. More specifically, this patent teaches a beverage comprising water, sugar, electrolytes, glycerol and pyruvate; and its use to ameliorate the effects of physical exertion. The teachings of U.S. Pat. No. 4,981,687 are incorporated herein by reference.

U.S. Pat. No. 5,089,477 discloses the use of pyruvate in a liquid composition that is used to prevent weight loss in agricultural animals resulting from dehydration.

U.S. Pat. No. 5,147,650 and U.S. Pat. No. 5,238,684 discloses and claims a fluid composition comprising water, electrolytes, sugar, glycerol, lactate and pyruvate. The teachings of U.S. Pat. Nos. 5,147,650 and 5,238,684 are incorporated herein by reference.

U.S. Pat. No. 5,236,712 discloses and claims a beverage containing water, electrolytes, pyruvate and alanine in a concentration of from about 0.5% to about 10%. The teachings of U.S. Pat. No. 5,236,712 are incorporated herein by reference.

Pyruvate in various forms has been proposed for enteral administration and for parenteral administration. Typically, pyruvates are available in the form of salts, for example, calcium pyruvate and sodium pyruvate. U.S. Pat. Nos. 5,283,260 and 5,256,697 disclose uses for the pyruvyl-amino acids and methods for their production.

Pyruvate has been administered to mammals enterally or parenterally typically at superphysiological levels. The amount of pyruvate administered generally ranges from 1 to 20% of the mammal's caloric intake. For enteral dosage, the pyruvate may be disbursed or dissolved in a beverage product or may be included in cookies, candies or other foods. Pyruvate may also be introduced as an aqueous solution parenterally.

The amino acid composition of numerous proteins, biologically active polypeptides and foods, has been known for some time. One pre-eminent monograph on this subject is the *Amino Acid Handbook* by Richard J. Block, C. C. Thomas, publisher, 1956 (Library of Congress Catalog Card No. 56-9104). On page 343 at Table II, the approximate amino acid composition of mammalian muscle proteins on average, is set forth as follows:

| Amino Acid | Grams/100 gm of Protein |
| --- | --- |
| Arginine | 6.6 |
| Histidine | 2.8 |
| Lysine | 8.5 |
| Tyrosine | 3.1 |
| Tryptophan | 1.1 |
| Phenylalanine | 4.5 |
| Cystine | 1.4 |
| Methionine | 2.5 |
| Serine | 5.1 |
| Threonine | 4.6 |
| Leucine | 8.0 |
| Isoleucine | 4.7 |
| Valine | 5.5 |
| Glutamic Acid | 14.6 |
| Aspartic Acid | 8.0 |
| Glycine | 5.0 |
| Alanine | 6.5 |
| Proline | 5.0 |
| Hydroxyproline | 4.7 |

On pages 272–273, the amino acid profile of human muscle tissue is set forth.

Protein supplementation for serious athletes, such as body builders, is well accepted. Typically recommended dosages range between 2.0 and 3.5 gms of quality protein per kilogram of body weight per day. Numerous sources for the protein supplements are known, such as milk, egg, soy, beef and vegetable protein. Isolated fractions of these sources are also known such as ion-exchange whey protein, caseinates, whey protein concentrates, immunoglobulin and egg albumin. Protein supplements typically are provided as powders or tablets. It is also known to provide protein supplementation in the form of peptides (hydrolyzed protein) or even free amino acids. These approaches have two major limitations; cost and taste. While the use of pyruvate is known for various medical indications and the use of protein supplements are known to increase muscle mass, the prior art has failed to recognize or even consider the combination of pyruvate with an anabolic protein composition. The anabolic protein composition of the present invention is prepared through the combination of various proteins, peptides or amino acid sources to arrive at an amino acid profile that parallels the amino acid profile of human muscle tissue. Consumption of the anabolic protein composition will result in an increase in muscle mass, less catabolism of muscle tissue after strenuous exercise or as a result of disease, and quicker muscle cell restoration. Even more surprising are the synergistic results that can be achieved when pyruvate is combined with the anabolic protein composition of this invention. An additional aspect of the present invention is that the anabolic protein composition alone or in combination with pyruvate can lessen the catabolic effects of diseases such as cancer and AIDS. The prior art has not disclosed or suggested the compositions and methods of the present invention.

DISCLOSURE OF THE INVENTION

There is disclosed an enteral composition comprising pyruvate and an anabolic protein composition. There is further disclosed an anabolic protein composition having an amino acid profile consisting essentially of: glutamic acid at about 12–17 weight %; lysine and leucine, each at about 7–11 weight %; valine, aspartic acid, alanine, threonine, serine, proline and phenylalanine, each at about 5–10 weight %; arginine, isoleucine and glycine, each at about 2–6 weight %; and tyrosine, histidine, tryptophan, cystine and methionine, each at about 0.5–5 weight %, based on the total amino nitrogen.

In a more preferred embodiment of the present invention, the anabolic protein composition comprises the following amino acids in the ranges recited based on 100 gm of protein:

| Amino Acid | Range in g/100 gm of Protein |
| --- | --- |
| Arginine | 2.7–5.5 |
| Histidine | 2.0–3.9 |
| Lysine | 7.0–10.1 |
| Tyrosine | 1.9–4.5 |
| Tryptophan | 1.0–2.7 |
| Phenylalanine | 5.0–8.0 |
| Cystine | 2.0–4.8 |
| Methionine | 1.8–2.5 |
| Serine | 5.0–8.5 |
| Threonine | 5.0–8.3 |
| Leucine | 9.0–11.0 |
| Isoleucine | 3.2–5.0 |
| Valine | 6.0–8.0 |
| Glutamic Acid | 12.0–17.0 |
| Aspartic Acid | 5.0–9.5 |
| Glycine | 2.2–4.5 |
| Alanine | 5.0–7.1 |

-continued

| Amino Acid | Range in g/100 gm of Protein |
|---|---|
| Proline | 6.0–8.2 |
| Hydroxyproline | 3.5–6.5 |

There is further disclosed a method for increasing the lean body mass or muscle mass of a mammal, said process comprising administering to a mammal in need of increased lean body mass or muscle mass, a composition comprising pyruvate and an anabolic protein composition. The present invention is also concerned with a method to ameliorate the catabolic effects of diseases such as cancer and AIDS. The method comprises the administration of the anabolic protein composition of the present invention with or without pyruvate. This invention is also concerned with the treatment osteoporosis by the administration of calcium pyruvate.

The present invention is also directed to a method of ameliorating the effects of physical exertion, said method comprising the administration to a person in need of such amelioration, a composition comprising pyruvate and an anabolic protein composition. The weight ratio of pyruvate to anabolic protein composition can range from about 1:1 to about 1:50. More preferably, the weight ratio of pyruvate to anabolic protein composition is 1:5 to 1:20. The amount of the pyruvate and anabolic protein composition administered to the mammal ranges from 1 to 300 gms per day. More preferred, the mammal should consume from 25 to 75 gms per day. On a weight to weight basis, the amount of the anabolic protein/pyruvate composition consumed by the mammal can range from 2.0 to 4.0 gms per kilogram of body weight per day.

Specific forms of pyruvate useful in the present invention include sodium pyruvate, magnesium pyruvate, calcium pyruvate, potassium pyruvate, pyruvyl-glycine, pyruvamines, pyruvyl-alanine, pyruvyl-leucine, pyruvyl-valine, pyruvyl-isoleucine, pyruvyl-phenylalanine, pyruvyl-proline, pyruvyl-sarcosine, their amides, esters and salts, and mixtures thereof The composition of the present invention may include other materials such as fats, carbohydrates, vitamins, minerals, sweeteners, flavoring agents and the like. For example, the synergistic composition of the present invention, pyruvate plus anabolic protein composition, may be combined with known food ingredients or dispersed in a liquid such as orange juice, and consumed orally.

In the method of the present invention, the mammal, preferably a human, consumes at least 25 gms per day of the pyruvate/anabolic protein composition. On a percent of calories basis, the synergistic combination can comprise from 1 to about 50% of total caloric intake.

In a preferred embodiment, the pyruvate is in the form of calcium, potassium or magnesium pyruvate or mixtures thereof and the anabolic protein composition comprises intact protein, hydrolyzate fractions and/or free amino acids, wherein 100 gms of said anabolic protein composition comprises 2.7 to 5.5 gms of arginine, 2.0 to 3.9 gms of histidine, 7.0 to 10.1 gms of lysine, 1.9 to 4.5 gms of tyrosine, 1.0 to 2.7 gms of tryptophan, 5.0 to 8.0 gms of phenylalanine, 2.0 to 4.8 gms of cystine, 1.8 to 2.5 gms of methionine, 5.0 to 8.5 gms of serine, 5.0 to 8.3 gms of threonine, 9.0 to 11.0 gms of leucine, 3.2 to 5.0 gms of isoleucine, 6.0 to 8.0 gins of valine, 12.0 to 17.0 gms of glutamic acid, 5.0 to 9.5 gms of aspartic acid, 2.2 to 4.5 gms of glycine, 5.0 to 7.1 gms of alanine, 6.0 to 8.2 gms of proline and 3.5 to 6.5 gms of hydroxyproline.

As used herein and in the claims, the term "amino nitrogen source", "source of amino nitrogen" or "anabolic protein composition" is meant to mean intact protein such as sodium caseinates, whey protein, soy protein, hydrolyzed proteins, fractions of hydrolyzed proteins, meat proteins, vegetable proteins, peptides, free amino acids and mixtures thereof. The anabolic protein composition useful in this invention can be a blend of numerous sources of amino nitrogen or of just a few. The required aspect of this invention is that the amino acid profile of the anabolic protein composition be as close as possible to the amino acid profile of human skeletal muscle tissue.

The present invention also contemplates the separate oral administration of the pyruvate and the anabolic protein composition. Therefore, dosages of each component can occur separately, provided both components are found systematically in the mammal prior and/or subsequent to strenuous exercise. The present invention also contemplates the use of genetically engineered plants, animals and/or organisms to produce the anabolic protein composition.

The inventive pyruvate/anabolic protein composition of this invention is also useful to increase the energy levels and general well being of a mammal. The inventive composition can be used as a food additive, i.e., added to pancake mix or consumed in the form of pills, candies, confections, capsules or powders.

In order to demonstrate the present invention, the following examples are submitted.

EXAMPLE I

Preparation of the Anabolic Protein Composition

One aspect of the present invention resides in the novel anabolic protein composition. This protein composition, which is based upon the amino acid profile of human muscle, provides the catabolic human (from strenuous exercise or disease) with the proper balance of amino acids to prevent degradation of lean body mass or to increase body protein concentration.

Those skilled in the arts of nutrition, protein chemistry and food science will appreciate that numerous sources of amino nitrogen can be blended to arrive at the claimed amino acid profile. Also contemplated within the scope of the present invention is the production of the anabolic protein composition through the use of recombinant or transgenic technologies. For example, a bacteria such as *E. coli* can be provided with a gene that encodes the production of the anabolic protein composition or a lactating mammal may have a gene inserted into its genome that produces the human muscle tissue protein. The anabolic protein would then be isolated from the milk and used in accordance with the present invention.

A representative anabolic protein composition according to the present invention was prepared by blending the following components at the recited percent by weight. The values have been corrected for actual percent of each raw material as to source of amino nitrogen.

| Ingredient | % by Weight |
|---|---|
| Whey Protein Concentration | 26.64 |
| Calcium Sodium Caseinate | 20.29 |
| High Protein Rice Flour | 21.01 |
| Meat Protein Concentrate | 15.02 |
| Egg White Solids | 13.00 |

-continued

| Ingredient | % by Weight |
|---|---|
| L–Leucine | 0.36 |
| L–Lysine | 2.17 |
| L–Arginine | 0.14 |
| L–glycine | 1.37 |

This representative anabolic protein composition was a blend of the following commercially available materials:

1) Whey Protein Concentrate: CALPRO 75
   A product of New Zealand Milk Products, Inc. at Petaluna, Calif.;
2) Calcium Sodium Caseinate: Alanate 220
   A product of New Zealand Milk Products, Inc. at Petaluna, Calif.;
3) High Protein Rice Flour
   A product of California Natural Products at Manteca, Calif.;
4) Meat Protein Concentrate: AMPRO 600
   A product of American Meat Protein Association at Ames, Iowa;
5) Egg White Solids: Type PF-1
   A product of Henningsen Foods, Inc. at Omaha, Nebr.; and
6) Amino Acids were obtained from various sources.

This blend of raw materials resulted in an amino acid profile as follows:

| Amino Acid | % by Wt. |
|---|---|
| Glutamic Acid | 16.6 |
| Leucine | 9.5 |
| Lysine | 7.0 |
| Valine | 6.0 |
| Arginine | 4.8 |
| Isoleucine | 5.0 |
| Aspartic Acid | 9.3 |
| Alanine | 5.7 |
| Threonine | 5.1 |
| Glycine | 3.1 |
| Serine | 5.5 |
| Proline | 6.8 |
| Phenylalanine | 5.0 |
| Tyrosine | 4.0 |
| Histidine | 2.8 |
| Tryptophan | 1.3 |
| Cystine | 1.9 |
| Methionine | 2.3 |

The raw materials were blended using standard techniques known in the industry. Calcium pyruvate was added to the anabolic protein to produce the inventive mixture used in Example II.

EXAMPLE II

Three groups of 10 rats each (Control, Control Pyruvate and Control Anabolic Protein Composition), each weighing about 200 gms, is fed a standard laboratory diet supplemented as described below, for a period of 60 days. The standard rat diet contains 15% protein, 28% fat and 57% carbohydrate. A fourth group of 10 rats (Experimental) is fed the same standard diet as the Controls, except for the addition of a mixture of calcium pyruvate and the anabolic protein composition. The anabolic protein composition is set forth in Example I. The mixture is 15% by wt. calcium pyruvate and 85% by wt. anabolic protein composition. The weight ratio of pyruvate to anabolic protein composition is thus 1:5.7. The Experimental group diet is a 90 wt. % blend of the standard diet with 10 wt. % of the inventive mixture. The Control diet is iso-energetically supplemented with maltose-dextrine and the electrolyte composition of the Control diet is made equal to the Experimental diet by adding appropriate amounts of calcium carbonate and sodium citrate. The Control Pyruvate diet contains the same amount of pyruvate as the Experimental and is iso-energetically supplemented with ion exchange whey protein to account for the missing anabolic protein composition. The Control Anabolic Protein Composition diet contains the same level of anabolic protein composition as the experimental and is iso-energetically supplemented with maltose-dextrine, calcium carbonate and sodium citrate to account for the missing pyruvate. Over the 60 day feeding period, the chow and water were provided ad libitum.

Data on diet consumption per day is collected and the animals are also weighed daily. On days 7, 21, 39 and 60 post feeding, the rats are evaluated for total body fat using the water tank method known to those skilled in the art. On day 7 post feeding, each rat is placed in an exercise cage driven by an electric motor. The speed of the exercise cage is set at 100 rpm. The time for each rat to fail to keep up with the set speed is measured. Failure to meet the set speed of the wheel is determined when the rat becomes inverted within the cage. The time to failure is a measure of endurance of the rat. This procedure of exercise to exhaustion is performed daily except for days 14, 21, 28, 35, 29, 46, 53 and 60.

The exercise cage data will indicate that the average time to exhaustion of the Experimental group is 30% greater than the Control and Control Anabolic Protein Composition groups. The Control Pyruvate rats will demonstrate an approximately 15% longer time to exhaustion than the Control and Control Anabolic Protein Composition rats. This is evidence that the inventive, synergistic composition increases endurance and/or performance in a mammal.

The total body fat data will indicate that the Experimental group has a 15% increase in lean body tissue (muscle) over all the Controls. The data will also indicate that the Experimental group gained 20% less fat than the Control and Control Anabolic Protein Composition groups.

There will be found a marked increase of protein concentration (muscle tissue) in the animals fed the composition of the present invention. The synergistic effect of the present invention provides for an increase in body protein concentration by providing the necessary amino acids for the regeneration and addition of muscle tissue while decreasing the deposition of body fat.

An additional important indicator of the novel synergistic composition's effectiveness has been a significant lowering of the perceived difficulty of long term exercise among individuals that consume the pyruvate/anabolic protein composition. The lower difficulty perceived by individuals receiving the pyruvate/anabolic protein composition of the invention will lead to enhanced physical performance, especially when long term exercise, such as marathons, are involved.

In one preferred embodiment of the present invention, there is provided a container or package containing a pharmaceutically acceptable mixture of pyruvate and anabolic protein composition in a unit dosage quantity (i.e., pills or capsules) together with instructions for administration of effective quantities over a period of time. In another embodiment, the synergistic composition of this invention is in combination with a liquid or powdered base, such as glucose, flavoring agents or carbohydrates to improve patient acceptance of the composition. The composition of this invention may also be incorporated as an ingredient in a foodstuff such as cookies, pretzels, candies, chewing gums, rehydration solutions and the like.

Industrial Applicability

The medical community and the serious athlete are constantly searching for compositions and methods that will enhance athletic performance and/or endurance while also increasing the lean body mass, protein concentration and muscle mass of the athlete. There is also a need for nutritional compositions that will assist the catabolic patient in maintaining weight or preventing further weight loss. Thus, the inventive anabolic protein composition of the present invention either alone or in combination with pyruvate will be useful for patients suffering from cancer or AIDS. There is also a need for compositions which reduce the deposition of body fat and reduce the catabolic effects of strenuous exercise. The present invention is based in part on the synergistic combination of a known chemical entity (pyruvate) and an anabolic protein composition which surprisingly produces outstanding increases in athletic endurance and performance while also increasing body protein concentration and muscle mass while lessening the deposition of fat in the body. The present invention will be of substantial benefit to all athletes, especially body builders, weight lifters, football players and the like.

Although the invention has been described in connection with certain specific embodiments, it will be readily apparent to those skilled in the art that various changes can be made to suit specific requirements without departing from the spirit of and scope of the invention.

We claim as our invention:

1. An anabolic protein composition having an amino acid profile consisting essentially of:

a) glutamic acid at about 12 to 17 weight %;

b) lysine and leucine each at about 7 to 11 weight %;

c) valine, aspartic acid, alanine, threonine, serine, proline and phenylalanine each at about 5 to 10 weight %;

d) arginine, isoleucine and glycine each at about 2 to 6 weight %; and e) tyrosine, histidine, tryptophan, cystine and methionine each at about 0.5 to 5 weight % based on the total amino nitrogen.

\* \* \* \* \*